United States Patent
Hummel et al.

US006413750B1

(10) Patent No.: US 6,413,750 B1
(45) Date of Patent: *Jul. 2, 2002

(54) (R)-SPECIFIC ALCOHOL DEHYDROGENASES FROM LACTOBACILLUS WITH IMPROVED CATALYTIC ACTIVITY USING AN NAD+ SUBSTRATE

(75) Inventors: Werner Hummel, Titz; Bettina Riebel, Frankfurt, both of (DE)

(73) Assignee: Forschungszentrum Jülich GmbH, Jülich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/447,125

(22) Filed: Nov. 18, 1999

Related U.S. Application Data

(63) Continuation of application No. PCT/DE98/00848, filed on Mar. 18, 1999.

(30) Foreign Application Priority Data

Mar. 19, 1998 (DE) .......................................... 198 12 004

(51) Int. Cl.⁷ ................................................. C12N 9/04
(52) U.S. Cl. ...................................................... 435/190
(58) Field of Search .......................................... 435/190

(56) References Cited

U.S. PATENT DOCUMENTS 6,037,158 A * 3/2000 Hummel et al. ............ 435/190

OTHER PUBLICATIONS

Hummel W. Enzyme–catalyzed Synthesis of Optically Pure R(+)–Phenylethanol. Biotechnol. Lett. (1990) 12(6):403–408.*
Rellos et al. Alteration of substrate specificity of Zymomonas mobilis alcohol dehydrogenase–2 using in vitro random mutagenesis. Protein Expr Purif (1997) Feb.;9(1):83–90.*
Scrutton et al. Redesign of the coenzyme specificity of a dehydrogenase by protein engineering. Nature (1990) Jan. 4;343(6253):38–43.*

* cited by examiner

*Primary Examiner*—Ponnathapu Achutamurthy
*Assistant Examiner*—Kathleen Kerr
(74) *Attorney, Agent, or Firm*—Klaus J. Bach

(57) ABSTRACT

In a method for improving the NADH specificity of preferred NADPH-dependent dehydrogenases, the alkalinity of the enzyme is reduced in the coenzyme docking area by an appropriate change of the amino acid sequence achieved by genetic engineering means. The inventive process is especially used for obtaining short-chain dehydrogenases with coenzyme binding areas on the N-terminus from *Lactobacillus brevis* and *Lactobacillus kefir*.

2 Claims, No Drawings

(R)-SPECIFIC ALCOHOL DEHYDROGENASES FROM LACTOBACILLUS WITH IMPROVED CATALYTIC ACTIVITY USING AN NAD+ SUBSTRATE

This is a continuation application of international application PCT/DE99/00848 filed Mar. 18, 1999 and claiming the priority of German application 198 12 004.4 filed Mar. 19, 1998.

BACKGROUND OF THE INVENTION

The invention comprises a process for improving the NADH-specificity of usually NADPH-dependent dehydrogenases which is useable particularly for obtaining dehydrogenases—specifically short-chain dehydrogenases and preferably alcohol-dehydrogenases—with an NADH-dependency corresponding to a $k_{cat}/K_M$-value for $NAD^+$ $\geq 20$ suitable for preparative purposes. It includes dehydrogenases obtained thereby and the use thereof.

Dehydrogenases, particularly alcohol-dehydrogenases, (below abbreviated as $ADH_n$) are valuable catalysts for obtaining chiral products by stereoselective reduction of prochiral ketones to the corresponding chiral alcohols. Commercially available are the corresponding enzymes from yeast (NAD-dependent), horse liver (AND-dependent) and *Thermoanaerobium brockii* (NADP-dependent) and also, for special substrates, for example steroid-dehydrogenases (NAD and NADP-dependent). Due to the quite limited substrate spectrum specifiy of these, additional new ADH's have become commercially available in the last years which are especially well suited for preparative uses, for example, an (S)-specific ADH from *Rhodococcus erythropolis* (NAD-dependent) or (R)-specific enzymes from the species Lactobacillus. Both types of enzymes catalize a variety of ketone conversions with a high enantioselectivity. The enzymes from *L. kefir* (DE 40 14 573) or *L. brevis* are of particular interest since they are unique in leading to (R)-alcohols. However, there is a disadvantage in the use of these enzymes in that they require the co-enzyme $NADP^+$ or respectively, NADPH since this co-enzyme is substantially less stable and more expensive (by a factor 5–10) than $NAD^+$, or respectively, NADH.

It is the object of the present invention to provide a method for improving the $NAD^+$ dependency of such ADHs, and which, moreover, is useable for improving dehydrogenases in general.

SUMMARY OF THE INVENTION

The initially mentioned inventive method which was developed for this purpose is characterized in that the bascity of the enzyme in the coenzyme-docking area is reduced by a suitable change in amino acid sequence using genetic engineering means. This reduction in basicity of the amino acid residues in the co-enzyme-docking area can be achieved particularly by an exchange of positively charged amino acid(s) for uncharged amino acid(s).

Alternatively, or additionally, the basicity of amino acids in the coenzyme docking area can be reduced by displacement of neutral or positively charged amino acid(s) with negatively charged amino acids. Of course, to achieve this reduction in basicity various combinations of these displacements are possible.

Further specialities of the invention are apparent from the patent claim and the following description.

The method is based on the fact that an acceptance of the coenzyme at the coenzyme-binding location is important for the participation of the coenzyme in the enzymatic redox-reaction and that the acceptance of $NAD^+$ as compared to $NADP^+$ can be improved by a reduction in basicity in the docking area of the enzyme through corresponding alterations of the amino acid sequence. Such alteration was done and examined by molecular engineering devices and a substantial improvement was achieved in this way as it will become apparent from the following description.

As a realization example, ADH from the Lactobacillus brevis (DSM 20 054) was used, wherein a coenzyme binding location in the N-terminus is assumed and whose sequence of the first 50 amino-acids in the N-terminal area is:

S-N-R-L-D-G-K-V-A-$I_{10}$-I-T-G-G-T-L-G-I-G-$L_{20}$-A-I-A-T-K-F-V-E-E-$G_{30}$-A-K-V-M-I-T-G-R-H-$S_{40}$-D-V-G-E-K-A-A-K-S-$V_{50}$. (SEQ ID NO 21).

The complete sequence of the ADH's subunit, which consists of four identical subunits, is published in the dissertation B. Riebel (1997, University of Düsseldorf), and also the corresponding DNA sequence which served as a template for the mutations.

In this N-terminal sequence certain basicity-relevant amino acids were exchanged by established genetic engineering devices and the changes in the acceptance of $NAD^+$ were determined basically with two values, the $K_M$ value and the $k_{cat}$ value. The $K_M$ value (Michaelis-Menten-constant [Mol/L]) can be considered to be a measure for the affinity of the co-enzyme to the enzyme. Preferably, the $K_M$ value is as small as possible. The $k_{cat}$ value (Mol formed product/mol enzyme×sec) is a measure for the conversion, it should be as high as possible. A combined value, which takes both values into consideration is the quotient $k_{cat}/K_M$. This should be preferably $\geq 20$ for obtaining an enzyme suitable for preparative purposes.

In the following examples 1–4 basic amino acids were replaced by neutral amino acids at the locations R38, H39, K45 and/or K48. Characterization of the mutants reveals that it is actually possible to change the ADH's coenzyme specificity (*L. brevis*) from $NADP^+$ towards $NAD^+$. Although only a limited number of amino acid exchanges were performed, the results show that the desired improvement of the $NAD^+$ dependency by basicity reduction can be achieved.

An exchange of A9G (Alanine for Glycine; both are uncharged) additionally performed in the following examples was not done in order to change the basicity but out of additional stability considerations. It can be clearly shown that the $NAD^+$ specificity changes, which were achieved by the exchange according to the invention for reducing the basicity, are not noticeably affected by the "accompanying exchange" (A96) as provided for in following examples.

Besides the inexaustive amino-acid exchanges performed close to the N-terminus area of the ADH from *L. brevis*, such an exchange can, of course, also be performed in the remaining amino acid chain (according to the above mentioned dissertation) and can be examined for a positive result with respect to the specificity for $NAD^+$.

In general, the method according to the invention of altering dehydrogenases requires the knowledge—or methods that lead to the determination—of the desired amino acid sequence which needs to be altered to improve a particular enzyme in order to permit the desired exchange of basic amino acids by uncharged or negatively charged amino acids or, respectively, an exchange of uncharged amino acids by negatively charged amino acids. The desired exchange area, which is useful for the improvement of the NAD-specificity, can be determined even with-out the previous knowledge of the coenzyme binding location—by way of trial-and-error. Site-specific mutagenesis has become far easier with the now commercially available ready-to-use kits for performing essential steps in genetic engineering procedures. In the case of basic amino acids, particularly lysine and argenine can be exchanged, preferably for uncharged amino acids, such as glycine, alanine, valine, leucine, isoleucine, methionine, serine, tyrosine, or phenylalanine. In the case of negatively charged amino acids, particularly glutamate acids and aspartic acids may be considered.

The successive changes of the mutated enzymes were proven by the determination of the kinetic parameters for the co-enzyme $NAD^+$, $NAPD^+$, NADH and NADPH by means of the corresponding kinetic parameters for the ketone substrate (acetophenone) or, respectively, by the oxidation reaction for the alcohol (phenylethanol). Furthermore, maintenance of the enantioselectivety was examined using the example of reduction of acetophenon. In addition, temperature-optima and stability, pH optima and stability and the iso-electric point were determined and compared with the corresponding data for the non-mutated wild-type enzyme.

The wild type enzyme has the following properties:

A) Kinetic Data for the Coenzyme $NADP^+$, $NAD^+$, NADPH and NADH (Table 1):

TABLE 1

Kinetic data for the oxidized and reduced coenzymes during reaction with the ADH from *Lactobacillus brevis*.

| Parameter | $K_M$ value [mM] | $K_{cat}$ value [sec$^{-1}$] | $K_{cat}/K_M$ mM$^{-1}$ sec$^{-1}$ |
|---|---|---|---|
| NADP$^+$ | 0.241 | 65 | 270 |
| NAD$^-$ | 2.938 | 21 | 7 |
| NADPH | 0.218 | 536 | 2461 |
| NADH | Not measurable | Not measurable | — |

Table 1 shows that the coenzyme NADH of the wild type of the ADH from *L. brevis* is not converted to an extent that it can e detected. Only very high concentrations of $NAD^+$ with a slight activity are accepted so that the selectivity ($k_{cat}/K_M$) of the wild type for $NAD^+$ (=7) in comparison with the value for $NADP^+$ (=270) is at about 2.5%.

B) Temperature-optimum and -stability

The temperature optimum of the wild type-ADH is around 55° C.; after a 24 hour incubation period at various temperatures, it still exhibits 100% residual activity at 30° C.; at 37° C. the residual activity is 50%.

C) pH Optimum and Stability

The pH optimum for the reduction of acetophenon with NADPH is 6.5. The optimum range is very narrow. Already at pH 6.0 or 7.0, there is only a residual activity of about 60%. For the oxidation of phenylethanol with $NADP^+$ the optimum is at about 8.0 with a wider optimum range of 7–9. The wild-type enzyme exhibits highest stability when stored at pH 7.0 to 8.5.

D) Determination of the Iso-electric Point.

The iso-electric point of the wild type enzyme is at 4.95.

E) Batchwise Reduction of Acetophenon Under Coenzyme Regeneration and Determination of the Enantioselectivity of This Conversion.

The reduction of acetophenon with NADPH using the wild type enzyme with coenzyme regeneration shows after gaschromatographic separation exclusively the (R) isomere of phenylethanol.

In the following examples, the generation and characterization of mutants is described in which amino acids in the N-terminal area are exchanged by molecular engineering devices.

EXAMPLE 1

Production and Characterization of the Mutant 1 (A9G, R38L, K45I)

The goal of this experiment was to mutate, in comparison to the wild type, the following three amino acid exchanges: Arginine(R) in the position 38 is to be exchanged for leucine (L) (R38L), lysine (K) in position 45 for isoleucine (I)(K45I) and alanine (A) in position 9 for glycin (G) (A9G). The mutant 1 can therefore be described incomparison to the wild type as follows: A9G, R38L, K45I.

A) Method of the Mutagenesis:

An essential methodical step in the generation of the mutants is the PCR (polymerase chain reaction) for amplifying DNA. Starting point is the DNA replication by DNA polymerases, which doubles the DNA in a first step using a predetermined template. By repeating this simple step, each newly produced and each old template becomes an original for a new replication. In this way, an exponential amplification is achieved (2").

Each single cycle of a PCR consists of three steps: a denaturing step at 94–96° C., where the double-stranded DNA melts to the single-stranded state, an annealing step at a selectable temperature where so-called primers can attach to the now single-stranded DNA, and a polymerase step at 72° C., (the usual temperature optimum of thermophilic polymerases), wherein these polymerases connect to the primers and complete the single strand to form again a double strand. Since this involves double-stranded DNA, primers must be added for both strands, the sense as well as the anti-sense strand. Correspondingly, these primers are called sense and anti-sense primers. Including all fusion-PCR steps, 52° C. is used as the annealing temperature; all other PCR steps for the generation of the mutants 1 and 2 occur at a temperature of 52° C., those for the mutants 1/1 and 2/2 at a temperature of 56° C.

These three steps can be repeated as often as desired, so that the same three steps are performed in a single reaction containment in the given order for the continuously increasing number of the present and the newly produced templates.

The primers mentioned above are necessary DNA recognition for the polymerase. They also determine the specificity of the PCR. With the predetermined primer sequence, the desired DNA sections are amplified. However, primers can bind only to the targeted DNA if they find a more or less complementary sequence in the targeted DNA. The complementary binding capacity is determined on one hand by the sequence homology and, on the other hand, by the annealing temperature in the second step of the PCR. The annealing temperature is derived from the primer's melting temperature.

In the present case, the PCR was used for the generation of the individual cofactor mutants. The point mutations in the target DNA were introduced by means of such primers, implying that in selected nucleotide bases the primers do not show a correct homology to the DNA sequence. As, inspite of point mutations, the homology of the primers was still 94%, the PCR was possible (at an average primer base length of 33 bases, 2 bases were exchanged).

The point mutations must be inserted at both strands of the double-stranded DNA for a correct change of the target sequence. This indicates that two individual PCR reactions are necessary for the introduction of a point mutation in the gene. In the first reaction from the 5' end of the gene (sense-primer) up to the mutation a PCR is performed; in the second reaction a PCR is performed starting at the mutation point up to the 3' end of the gene (in anti-sense direction).

If several point mutations are to be initiated whose distances relative to each other exceed the finite length of a primer (40–60 bases) the above mentioned two PCR-reactions must be performed separately for each point mutation.

If such point mutations are introduced by PCR, a complete gene is not present from the beginning, just parts resulting from the individual reactions, the 5' end up to the mutation and the section of the mutation up to the 3' end. They must be fused by a so-called fusion PCR to a complete gene.

Fusion-PCR:

The principle of this PCR corresponds to the one described above; but in this case two different templates are added which have a 100% homology in the mutation area specific for the length of the earlier introduced mutation primer (generally about 30–40 bases). This mutation area acts, because of it homology, as a primer of the fusion PCR, so that, after denaturization of the DNA into the single strands, the two original strands can come together again in the subsequent annealing step; but also the two different strands in the homology area may pair up. The polymerase may then complete the remaining DNA to a double strand from the mutation area as the primer. In order to allow only this possibility, no gene-specific primers are added during the fusion PCR in the first 5–10 cycles.

After 5–10 cycles, sufficient complete gene DNA is available, so that, after the addition of the 5' and 3' gene-specific primer, the gene is amplified in the following cycles. The earlier added gene pieces cannot be amplified since only one primer is available for each counter part (either only the sense or the anti-sense). Only the gene completed in the first cycles can be amplified with both gene-specific primers.

The first mutant generated by this method contains, in comparison with the wild type enzyme, three amino acid exchanges: Arginine (R) in the position 38 was exchanged for leucine (L) (R38L), lysine (K) in position 45 was exchanged for isoleucine (I) (K45I) and (not specific to the invention) additionally alanine (A) in position 9 was exchanged for glycine (G) (A9G).

The procedure for achieving this mutant was carried out as described below:

As a template for the generation of the point mutation gene fragments, recombinant plasmid [recADHpkk-177-3H] was used from which the ADH-gene (recADH) was cut out by the use of restriction endonucleases EcoR1 and Hind III. After elution out of an agarose gel the restricted fragments were used in PCR. As primer for the generation of the mutation the following were used:

R38LK 46I (SEQ ID NO. 3): acc ggc ctg cac agc gat gtt ggt gaa ata gca gct (36 bp) (mutation-primer sense) and BRAS (SEQ ID NO. 2): gcgc aag ctt cta cta ttg agc agt gta gcc acc gtc aac tac aaa ttc aga (3' primer antisense), which counts for the big gene fragment B; as well as BRS (SEQ ID NO. 1): gcgc gaa ttc atg tct aac cgt ttg gat ggt (5'-primer sense) and R38LK46Irev (SEQ ID NO 4): agc tgc tat ttc acc aac atc gct gtg cag gcc ggt (3'-primer anti sense), which counts for the small gene fragment A; as well as All primers are always presented in the 5'→3'-reading frame, the primers BRS and BRAS correspond to the 5' or, respectively, 3' ends of the recADH gene. The components and concentrations used in each case are listed in table 2.

TABLE 2

PCR preparations (dNTP = 0.2 mM of each of dTTP, dATP, dCTP and dGTP; buffer (start solution) = 100 mM Tris/HCL pH 8.8; 15 mM MgCl$_2$; 500 mM KCl; 1% triton X-100(v/v); DNAzyme = Biometra-polymerase). The explanations of the abbreviations are identical for all the following tables with PCR preparations.

| PCR | Template | 5'primer | 3'-primer | NTP [mM] | Buffer | DNAzyme |
|---|---|---|---|---|---|---|
| 1 | recADH 100 ng | 100 pmol R38LK46I | 100 pmol BRAS | 0.2 | 10 µl | 1 µl |
| 2 | recADH 100 ng | 100 pmol BRS | 100 pmol R38LK46Irev | 0.2 | 10 µl | 1 µl |

Depending on the volume of the added substances, water is added to the reaction mixture to provide a volume of 100 µl; this is valid for all PCR preparations below.

The PCR-fragments were purified and combined through the overlapping homogenous part in a fusion PCR (table 3) to the complete gene containing the point mutations.

TABLE 3

PCR-preparation (abbreviations see table 2):

| PCR | Template | 5'primer | 3'-primer | dNTP [mM] | Buffer | DNAzyme |
|---|---|---|---|---|---|---|
| 3 | Fragments from PCR 1 and 2 | 100 pmol BRS | 100 pmol BRAS | 0.2 | 10 µl | 10 µl |

The fragment amounts depend on the size of the fragments. For the fusion PCRs equal pmol amounts must be present at the free ends of the fragments, to be precise, with the same concentration in ng, smaller fragments have a larger count of pmol ends than larger fragments. For mutant 1, the ratio is 1:4.4 (small to large fragment), so that 4.4 times fewer small fragments need to be used than large fragments.

Introduction of the third mutation A9G:

A9G: ggt aag gta gga atc att aca (5' primer) and

BRAS: (3' primer), which result in the large fragment.

BRS (5' primer) and A9 Grev: tgt aat gat tcc tac ctt acc (3' primer), being the two primers which result in the small fragment (substances and concentrations, see table 4).

TABLE 4

PCR preparation (abbreviations see table 2):

| PCR | Template | 5' primer | 3' primer | DNTP [mM] | Buffer | DNAzyme |
|---|---|---|---|---|---|---|
| 4 | product of PCR 3; 100 ng 100 ng | 100 pmol A9G | 100 pmol BRAS | 0.2 | 10 µl | 1 µl |
| 5 | Product of PCR 3 100 ng | 190 pmol BRS | 100 pmol A9Grev | 0.2 | 10 µl | 1 µl |

The amplified fragments are again fused together through fusion PCR (Table 5).

TABLE 5

PCR preparation

| PCR | Template | 5' primer | 3' primer | NTP [mM] | buffer | DNAzyme |
|---|---|---|---|---|---|---|
| 6 | Fragments of PCR 4 and 5 | 100 pmol BRS | 100 pmol BRAS | 0.2 | 10 μl | 1 μl |

The fragments were at the ratio 1:14.5 (small to large) The product of this PCR represents the mutant 1; it was cloned after purification into the expression vector pkk-177-3H, transformed and over-expressed in *E. coli* Hb101+ (pUBS520). The mutated gene can, of course, be inserted into vectors other than the pkk-177-3H also, for example, pBTac (company Boehringer, Mannheim), pKK-233 (Company Stratagene) or pET (Company Novagen). Correspondingly, *E. coli* strains other than HB101+ (pUBS520) may be used as host organisms such as *E. coli* NM522, *E. coli* RR1, *E. coli* DH5α or *E. coli* TOP 10⁻, which can be obtained from official strain collections or vector marketing companies.

B) Enzyme Production:

Cell Proliferation:

The cell mass for the preparation/production of the various mutants was always achieved through 5 L shaking flask fermentation; the HB101+ strain was always used as the host for the mutated recADH plasmides, so that, for fermentation, a doubled selection pressure by ampicillin and neomycin is needed. After growth in a liquid fermentation culture (1% trypton, 0.5% yeast extract, 1% NaCl, pH 7.5) at 37° C. up to an $OD_{550}$ of 0.5, the enzyme was induced by addition of 1 mM IPTG. After additional 4 h hours of growth, the cells were harvested and the gene expression was examined after crude extract preparation by activity determination and SDS-PAGE of the proteins. Alternatively, the cells obtained by fermentation may be stored frozen at −20° C.

Crude Extract Preparation Through Ultrasonic Method:

For the release of the enzyme, standard decomposition methods can be used. In this case, the recombinant organisms were decomposed by pulsed ultrasound. The cells resuspended in Tris buffer (0.1 M Tris-HCl, pH 7.5; 1 mM $MgCl_2$) were subjected to a decomposition procedure with 2×25 sec cycles at 30 sec intervals for cooling with a pulsed sonifier (company Branson) at 25% intensity. The decomposed cells were centrifuged and the supernatant was removed by pipette, called raw extract below.

As the following characterization will elucidate, this mutated enzyme (mutant 1) is relatively stable especially in comparison with enzyme from mutant 2.

Purification of the Enzyme from Mutant 1:

To obtain purified enzyme, standard procedures for the protein purification were used. Three purification steps using chromatography with phenylsepharose 6 FF, Q-sepharose FF and octyl sepharose FF (all commercially available products of the company Pharmacia, Freiburg) were applied. Table 6 summarizes the activities and the yields of the purification steps.

TABLE 6

Purification of the mutant 1:

| Purification step | Activity [U/min] | Spec. activity [U/mg] | Yield [%] | Purification factor | Total activity [U] |
|---|---|---|---|---|---|
| Crude extract | 13 | 0.9 | 100 | 1.0 | 390 |
| Phenyl sepharose | 13 | 7.4 | 69 | 8.5 | 269 |
| Q-sepharose | 71 | 25.0 | 64 | 29.0 | 252 |
| Octyl sepharose | 53 | 53.0 | 20 | 62.0 | 80 |

C) Determination of Kinetic Parameters

The characterization of the ADH mutant 1 with respect to the kinetic data resulted in the following values, which are combined in Table 7.

TABLE 7

Kinetic data for the enzyme mutant 1.

| Parameter | $K_M$ value [mM] | $K_{cat}$ value [sec⁻¹] | $K_{cat}/K_M$ mM⁻¹ sec⁻¹ |
|---|---|---|---|
| NADP⁺ | 0.254 | 114.8 | 451 |
| NAD⁺ | 1.823 | 79.8 | 44 |
| NADPH | 0.149 | 156.0 | 1046 |
| NADH | 0.179 | 17.7 | 99 |

In comparison to the wild type, this mutant shows already a clear improvement in the reactivity with respect to the coenzyme NAD⁺: The $K_M$ value is reduced significantly from 2.9 to 1.8 mM; at the same time the activity ($k_{cat}$) increased from 21 to almost 80. Both improvements, together, show that this mutant already accepts NAs substantially better. While the selectivity ($k_{cat}/k_M$) of the wild type for NAD⁺ in comparison to NADP⁺ is only about 2.5%, this value has increased to about 10% with the mutant 1.

D) Temperature-optimum and -stability

The optimal temperature was determined for reductive reactions at pH 7.0 with the two coenzymes NADH and NADPH to be 55° C. in both cases. The temperature stability was determined as residual activity after 25 h incubation at various temperatures. At 37° C., still 95% reactivity was obtained; at 42° C. still 34%.

E) pH Optimum and Stability

For determining the optimal pH value, the following buffers were used: pH 4.5=Na-acetate; pH 5.0 and 5.5=Na-acetate; pH 6.0 and 6.5=Kpi or MES; pH 7.0 and 7.5=Kpi or TEA; pH 8.0 and 8.6=Tris; pH 9.0=Bicine. All buffers were used in a concentration of 100 mM. For the determination of the reductive reaction 10 mM acetophenon was added. The concentrations of NADP/NAD were each 2 mM. The concentration of NADH/NADPH was each 0.25 mM. For measurement, 970 μl of the respective buffer solution, which already included substrate at the desired concentration, was mixed with 20 μl of the start solution with the desired co-enzyme. The reaction was started with 10 μl enzyme. the dilution factor depended on the activity, it was chosen in the range of 1 to 3 U/ml.

The pH-optima of the mutant for the reductive reaction was measured to be the same when using NADH or NADPH (in the acid range between 5.0 and 6.0). In comparison to that pH 7.5, an activity of only 4% was measured. For the oxidative reaction with NAD and NADP, a maximum activity was obtained at a pH value of 7.0.

The pH stability is expressed as residual activity after a 25 hour incubation period at various pH values, the same buffers were used as for the determination of the pH optima.

45 µl of the respective buffer were mixed with 5 µl of the enzyme solution and incubated at room temperature. Samples were taken after 30 min, 60 min., 6 hours and 25 hours.

With the mutant 1, the highest reactivity (100%) at storage at pH 5.0 was obtained. Already changes in pH 5.5 resulted in a residual activity of only 80% and a pH 7.0 resulted in a residual acitivity of only 34% after a 25 h period.

F) Determination of the Isoelectric Point

The isoelectric point (IP) is determined by isoelectric focussing (IEF) to be at pH 4.28. This is noteworthy particularly in comparison with the mutant 2 (see example 4). With the mutant 2, the IP is determined at 4.65 despite the fact that, in each of the two mutants, the same type of aminoacid (lysine) was exchanged; in mutant 1, it was the lysine-45 (to isoleucine) and in mutant 2, it was the lysine-48 (to methionine).

G) Batchwise Reduction of Acetophenone with Coenzyme Regeneration and Determination of the Enantioselectivity of this Conversion.

In the batch preparation of reduction of acetophenone with coenzyme regeneration using isopropanol, a complete conversion to phenylethanol has been achieved. In this case, 960 µl triethanolamine buffer, 50 mM, pH 7.0 with 11 mM acetophenon, 10 µl magnesium chloride (100 mM start solution); 25 µl $NADP^+$ (10 mM start solution), 9.4µl isopropanol, and 1 U alcohol dehydrogenase were used. The determination of the enantiomere purity obtained by gas chromatography in a sample after complete conversion (4 h) indicates that only the (R)-alcohol was obtained; (S) phenylethanol was not detectable.

EXAMPLE 2

Production and Characterization of the Mutant 1/1 (A9G, R38L, K45M)

It was the aim of the mutation to change the lysine in position 45 to methionine instead of isoleucin (mutant 1) and to compare it with mutant 1. The other changes made in mutant 1 in positions 9 and 33 have been maintained so that mutant 1/1 can be described in comparison to the wild type as follows:

A9G, R38L, K45M.

A) Recovery of Mutant 1/1

For the recovery of mutant 1/1, the same methods were used as described in example 1. Since the mutant 1/1 is an extension of the mutant 1, the mutant 1 is used as a template for the subsequent PCR.

R38LK45M (SEQ ID NO. 7): acc ggc ctg cac agc gat gtt gaa atg gca (5' primer) and BRAS (3' primer), which produce the large fragment.

BRS (5' primer) and R38LK45Mrev (SEQ ID NO 8): tgc cat ttc acc aac atc gct gtg cag gcc ggt (3' primer) which count for the small fragment.

TABLE 8

| | | PCR - preparation | | | |
|---|---|---|---|---|---|
| PCR | Template | 5' primer | 3' primer | NTP[mM] | Buffer | DNAzyme |
| 7 | product of 6; 100 ng | 100 pmol R38LK45M | 100 pmol BRAS | 0.2 | 10 µl | 1 µl |
| 8 | Product of 6 100 ng | 100 pmol BRS | 100 pmol R38LK45Mrev | 0.2 | 10 µl | 1 µl |

The fragments were purified and fused together in the fusion-PCR.

TABLE 9

| | | PCR preparation, fusion PCR: | | | | |
|---|---|---|---|---|---|---|
| PCR | Template | 5' primer | 3' primer | NTP [mM] | Buffer | DNAzyme |
| 9 | fragments of PCR 7 and 8 | 100 pmol BRS | 100 pmol BRAS | 0.2 | 10 µl | 1 µl |

The fragments were introduced into the fusion PCR at a ratio of 1:4.4. The product represents the mutant 1/1 since the mutation A9G was taken over from the mutant 1.

Like in mutant 1, the imported mutations were also here confirmed by sequencing of the gene. For the recovery of the enzyme mutant, the gene was overexpressed in *E. coli* HB101+ (pUBS520).

B. Enzyme Production

Fermentation and celldisruption were carried out according to the procedure described in example 1.

Purification of the Enzyme Mutant 1/1:

The purification of this mutated enzyme corresponds to the method described in example 1. Table 10 summarizes the characteristic data.

TABLE 10

| Purification of the enzyme mutant 1/1: | | | | | |
|---|---|---|---|---|---|
| Purification step | Activity [U/min] | Spec. activity | Yield [%] | factor | Total activity |
| Crude extract | 178 | 14 | 100 | 1 | 2470 |
| Phenyl sepharose | 137 | 81 | 64 | 6 | 1576 |
| Q-sepharose | 179 | 75 | 29 | 6 | 716 |
| Octyl sepharose | 140 | 100 | 11 | 7 | 280 |

C) Determination of the Kinetic Parameter for the Enzyme Mutant 1/1:

The characterization of the ADH mutant 1/1 with respect to the kinetic data for the coenzyme resulted in the values assembled in the following table:

TABLE 11

| Kinetic data for the oxidized and reduced coenzyme using enzyme mutant 1/1. | | | |
|---|---|---|---|
| Parameter | $K_M$ value [mM] | $K_{cat}$ value [$sec^{-1}$] | $K_{cat}/K_M$ [$mM^{-1} sec^{-1}$] |
| $NADP^+$ | 0.502 | 33.3 | 66 |
| $NAD^+$ | 0.502 | 33.3 | 66 |

TABLE 11-continued

Kinetic data for the oxidized and reduced coenzyme using enzyme mutant 1/1.

| Parameter | $K_M$ value [mM] | $K_{cat}$ value [sec$^{-1}$] | $K_{cat}/K_M$ [mM$^{-1}$ sec$^{-1}$] |
|---|---|---|---|
| NADPH | 0.352 | 166.4 | 473 |
| NADH | 0.188 | 10.3 | 55 |

Kinetic data show that the mutant accepts the coenzyme NAD$^-$ as well as NADP. The KM value for NAD$^+$ went down significantly; it is low at 0.5 mM instead of 2.9 for the wild type. As a consequence this mutant already shows an extremely good, low affinity to the co-enzyme NAD$^+$. Also, the $k_{cat}$ value is slightly improved; it is at 33.3 sec$^{-1}$. The comparison of the selectivities ($k_{cat}/K_M$) for both coenzymes shows for NAD$^+$ the same value of 66 mM$^{-1}$ sec as for NADP$^+$. In comparison to the wild type, which converts NAD$^+$ at a rate of 2.5% based on the NADP$^+$ value, the NAD$^+$ is converted at a rate of 100% by this mutant.

D) Temperature Optimum and Stability

The temperature optimum for the enzyme mutant 1/1 measured with NADPH is at least about 65° C.; higher temperatures could not be achieved for technical reasons. If the temperature optimum is determined with the co-enzyme NADH, the optimum value was found to be about 40° C. Presumably, the NADH is not bound as well to the enzyme at higher temperatures so that the activity is lower then. The measurement of the temperature stability shows that, after 25 hours at only 25° C., a residual activity of 100% is still present, at 30° C. it remains only 59%. There, the temperature stability of the mutant 1/1 is significantly deteriorated in comparison with the wild type enzyme.

E) pH Optimum and Stability

The pH optimum for the reduction direction (measurement with acetophenone) is determined at 6.0 for both coenzymes NADPH as well as with NADH. For the oxidation, the optimum is at 7.0 (NADPH$^+$) or respectively, 7.5(NAD$^+$).

F) Determination of the Isoelectric Point

The isoelectric point of the enzyme mutant 1/1 was determined at 4.85.

G) Batchwise Reduction of Acetophenone with Co-enzyme-regeneration and Determination of the Enantioselectivity of this Conversion.

The reduction of acetophenone under conditions as described in the example 1 provided only the (R) isomere of phenyl ethanol.

EXAMPLE 3

Production and Characterization of the Mutant 2 (A9G, R38L, K48M)

The aim of this mutation was to exchange the lysine in position 48 by methionine, in comparsion with mutant 1—instead of the K45I exchange described in the example of mutant A. The other exchanges occurring in the mutant 1 in position 9 and 38 have been maintained so that the mutant 2 can be described in comparison with the wild type as: A9G, R38L, K48M.

A) Method of the Mutagenesis:

For production of the mutant 2, basically the same methods were used as described in example 1. Since the mutant 2 was produced independently of mutant 1, the gene of the wild type—ADH(recADH) was again used as a template.

R38LK48M (SEQ ID NO 9): acc ggc ctg cac agc gat gtt ggt gaa aaa gca gct atg agt gtc (5' primer) and BRAS (3' primer), which yield the large fragment;
BRS(5' primer) and
R38LK48Mrev (SEQ ID NO 10): gac act cat agc tgc ttt ttc acc aac atc gct gtg cag gcc ggt (3' primer), which yield the small fragment.

TABLE 12

PCR-preparations

| PCR | Template | 5' primer | 3' primer | NTP [mM] | Buffer | DNAzyme |
|---|---|---|---|---|---|---|
| 13 | recADH 100 ng | 100 pmol R38LK48M | 100 pmol BRAS | 0.2 | 10 µl | 1 µl |
| 14 | recADH 100 ng | 100 pmol BRS | 100 pmol R38LK48Mrev | 0.2 | 10 µl | 1 µl |

The fragments were purified and used for the fusion-PCR.

TABLE 13

Fusion-PCR preparation

| PCR | Template | 5' primer | 3' primer | NTP [mM] | Buffer | DNAzyme |
|---|---|---|---|---|---|---|
| 15 | Fragments of PCR 13 and 14 | 100 pmol of BRS | 100 pmol of BRAS | 0.2 | 10 µl | 1 µl |

The fragments were used at a ratio of 1:44. The product of this fusion-PCR is an intermediate product of the mutant 2 since the mutation A9G was to be inserted in the next step.

Introduction of the third mutation A9G:

A9G (SEQ ID NO 5): ggt aag gta gga atc att aca (5' primer) and BRAS: (3' primer), which yield the large fragment;
BRS: (5' primer) and A9Grev (SEQ ID NO 6): tgt aat gat tcc tac ctt acc (3' primer), which yield the small fragment (Table 14).

TABLE 14

PCR preparation

| PCR | Template | 5' primer | 3' primer | NTP [mM] | Buffer | DNAzyme |
|---|---|---|---|---|---|---|
| 16 | product of 15: 100 ng | 100 pmol A9G | 100 pmol BRAS | 0.2 | 10 µl | 1 µl |
| 17 | product of 15 100 ng | 100 pmol BRS | 100 pmol A9Grev | 0.2 | 10 µl | 1 µl |

The fragments were used for fusion PCR at the ratio 1:1.45 (table 15)

TABLE 15

PCR-preparation

| PCR | Template | 5' primer | 3' primer | NTP [mM] | Buffer | DNAzyme |
|---|---|---|---|---|---|---|
| 18 | Fragments of PCR 16 and 17 | 100 pmol BRS | 100 pmol BRAS | 0.2 | 10 µl | 1 µl |

The product of this fusion PCR generates mutant 2. This mutant was cloned into the expression vector pkk-177-3H like all the other mutants. For obtaining the enzyme mutant, the gene was then over-expressed in *E. coli* HB101+ (pUBS520).

B) Enzyme Production:
Fermentation and Cell Disruption:
Fermentation, cell disruption and enzyme purification correspond to the procedure as described in connection with example 1. The table 16 comprises the characteristic data of the purification.

TABLE 16

Purification of the enzyme mutant 2:

| Purification step | Activity [U/ml] | Spec. activity [U/mg] | Yield [%] | factor | Total activity |
|---|---|---|---|---|---|
| Crude extract | 310 | 18 | 100 | 1 | 3300 |
| Heat precipitation | 330 | 35 | 100 | 2 | 3300 |
| Phenyl sepharose | 73 | 91 | 11 | 5 | 365 |
| Q-sepharose | 90 | 65 | 8.2 | | 270 |

C) Determination of the Kinetic Parameters of the Mutant Enzyme 2 (ADH):

The characterization of the ADH mutant 2 with respect to the kinetic data for the coenzyme resulted in the following values included in the table 17:

TABLE 17

Kinetic data for the oxidized co-enzymes for the mutant enzyme 2.

| Parameter | $K_M$ value [mM] | $k_{cat}$ value [sec$^{-1}$] | $k_{cat}/K_M$ mM$^{-1}$ sec$^{-1}$ |
|---|---|---|---|
| NADP$^+$ | 6.155 | 47.0 | 8 |
| NAD$^+$ | 0.619 | 33.1 | 54 |

In this mutant both parameters are changed with respect to NAD$^+$ advantageously in comparison to the wild-type. The KM value dropped from 2.9 to 0.62 mM, the $k_{cat}$ value improved from 21 to 33. As a consequence, the $k_{cat}/K_M$-value increased from 7.3 to 5.4. At the same time, particularly the affinity to NADP$^+$ ($K_M$-value), but also the $k_{cat}$-value become drastically worse so that this mutant preferably uses NAD$^+$ as coenzyme.

D) Temperature Optimum and Stability

The temperature optimum is significantly lower than with the wild type enzyme. Measured with NADP, it is 50° C., with NAD$^+$ at 33–37° C. Temperature stability shows 100% residual activity only at 25° C. after 25 h incubation, at 30° C., only 40% remained.

E) pH Optimum and Stability

The pH optimum for the reduction of acetophenon measured with NADPH is at 8.0; however, using NADH it lies at 6.5. This optimum at 6.5 corresponds to that of the wild type enzyme, measured with NADPH. Like the wild type enzyme also the activity measured with NADH shows only a narrow activity range. At pH 7.0, there is only a 46% residual activity left. The stability of the enzyme mutant at various pH values after 25 hrs shows maximum activity with pH 7.0; with pH 6.0 and also with pH 8.0 only 84% residual activity was measured after 25 h.

F) Determination of the Isoelectric Point.

The isoelectric point of the enzyme mutant is at pH 4.65.

G) Batchwise Reduction of Acetophenone with Coenzyme-regeneration and Determination of the Enantioselectivity of this Conversion.

The reduction of acetophenone under the same conditions as described in example 1 just gave the (R)-isomere of phenylethanol.

EXAMPLE 4

Production and Characterization of the Mutant 2/2 (A9G, R38L, H39L, K48M)

It was the objective of this mutation to introduce an additional amino acid exchange in comparison to mutant 2, by changing the basic amino acid histidine in position 39 into a neutral amino acid, the leucite. The mutant 2/2 can be described with reference to the wild-type as: A9G, R38L, H39L, K48M.

A), Method of the Mutagenese:

To obtain the mutant 2/2, the same methods were used as described in example 1.

Since. the mutant 2/2 represents a successor mutant of the mutant 2, this mutant was inserted as template for the PCR.

R38LH39L (SEQ ID NO. 11): acc ggc ctg ctc agc gat gtt (5' primer) and BRAS (3' primer), which yield the large fragment;

BRS (5' primer) and R38LH39Lrev (SEQ ID NO 12): aac atc gtc gag cag gcc ggt (3' primer), which yield the small fragment.

TABLE 18

PCR preparations

| PCR | Template | 5' primer | 3' primer | NTP [mM] | Buffer | DNAzyme |
|---|---|---|---|---|---|---|
| 19 | product of PCR18 100 ng | 100 pmol R38LH39L | 100 pmol BRAS | 0.2 | 10 µl | 1 µl |
| 20 | Product of PCR18 100 ng | 100 pmol BRS | 100 pmol R38LH39Lrev | 0.2 | 10 µl | 1 µl |

The fragments were purified and inserted into the fusion PCR at a ratio of 1:4.4 (small to large).

TABLE 19

Fusion PCR

| PCR | Template | 5' primer | 3' primer | NTP [mM] | Buffer | DNAzyme |
|---|---|---|---|---|---|---|
| 21 | fragments of PCR 19 and 20 | 100 pmol BRS | 100 pmol | 0.2 | 10 µl | 1 µl |

The product of this fusion PCR represents the complete mutant 2/2; the mutations K48M and A9G were taken over from the mutant 2. For obtaining the enzyme mutant, the gene was then over-expressed in *E. coli* HB101+ (pUBS520).

B) Enzyme Production

Fermentation, Cell Disruption and Purification of the Enzyme Mutant 2/2:

The enzyme production and the production of this mutated enzyme correspond to the method described in example 1. Table 20 comprises the characteristic data of the enzyme purification.

TABLE 20

Purification of the enzyme mutant 2/2

| Purification step | Activity [U/ml] | Spec. activity [U/mg] | Yield [%] | factor | Total activity |
|---|---|---|---|---|---|
| Crude extract | 35 | 1.9 | 100 | 1 | 467 |
| Heat Precipitation | 30 | 3 | 96 | 1.6 | 450 |
| Phenyl sepharose | 72 | 26 | 98 | 14 | 457 |
| Q-sepharose | 80 | 89 | 85 | 47 | 398 |
| Octyl sepharose | 65 | 93 | 28 | 49 | 130 |

D) Determination of the kinetic parameter for the enzyme mutant 2/2:

The characterization of the ADH mutant 2/2 with respect to the kinetic data resulted in the following values listed in table 21:

TABLE 21

| Parameter | Km value [mM] | $K_{cat}$ value [sec$^{-1}$] | $K_{cat}$/KM mM$^{-1}$ sec$^{-1}$ |
|---|---|---|---|
| NADP$^+$ | 0.143 | 30.8 | 215 |
| NAD$^-$ | 0.955 | 23.2 | 24 |
| NADPH | 0.370 | 101.1 | 273 |
| NADH | 0.070 | 33.6 | 479 |

In comparison with the wild type enzyme for NAD$^+$ the $K_M$ value of 2.9 dropped to 0.96 mM. For NADP$^+$, the $K_M$ as well as the $k_{cat}$ value deteriorated slightly.

The particularly good affinity of the mutant with respect to NADH is striking; the $K_M$ value is about 0.07 mM.

D) Temperature Optimum and Stability

The temperature optimum of the mutant 2/2, measured at pH 5.0 amounts to 42° C. as measured with NADPH and using NADH at 50° C. These optima are relatively widespread. Using NADPH, the activity is still 95% when measured at 50° C. Using NADH as the coenzyme at 60° C., the activity remains 70%. The stability for storage (6 h) at various temperatures shows for 30° C. still 67% and for 37° C. only 7%.

E) pH Optimum and Stability

The pH optimum for the reduction of acetophenone with NADPH amounts to 6.0; using NADH, it is at 5.0. Particularly with NADH, this mutant is actually active only in the acid range. At pH 7.0, the activity remains only 6% in comparison with the value at pH 5.0. For the oxidative direction as well, the optimum is slightly but significantly in the acid range. Maximum activity is at pH 7.5 with NADP$^+$ as well as with NAD$^+$. At pH 8.0, which is the optimum for the wild type, the activity amount for only 77% (NADP$^+$), or respectively, 61% (NAD$^+$). If the enzyme is stored at different pH values and the residual activity is measured after 6 h, there is still 100% residual activity at pH 7.0. At pH 8.5, the residual activity amount for only 58%.

F) Determination of the Isoelectric Point

The isoelectric point of the enzyme mutant 2/2 is about 4.47.

G) Batchwise Reduction of Acetophenone During Coenzyme Regeneration and Determination of the Enantioselectivity of this Conversion.

The reduction of acetophenone under the conditions as described in the example 1 showed the (R) isomere of phenylethanol only.

The examples 1 to 4 show that the basicity reduction in the coenzyme-relevant amino acid sequence area of the ADH protein of the NADP-preferring alcohol dehydrogenase of *lactobacillus brevis* by a genetic engineering change of basic to uncharged amino acid rests such as R38L, H39L, K45I, K45M, or respectively, K48M in different conditions leads to a praxis-relevant improvement of the NAD specificity of the enzyme.

Such an exchange of basic for uncharged amino acid rests in the coenzyme sensitive or respectively, in the co-enzyme docking area for the NAD$^+$ specificity improvement is of course possible in an analog manner with other dehydrogenases whose amino acid or DNA sequences are already known or still to be determined. The coenzyme-sensitive variation can be recognized by the successful changes in the case of not knowing the specific area.

For instance, in other NADP-preferring dehydrogenases, amino acid sequences are known and can be searched in data banks wherein preferably the search may first be directed to the similarity area of an already known coenzyme binding motif.

In the present case, enzymes were searched for in the protein sequence data bank ("Swiss-Prot"), which have similarities with the sequence of the *L. brevis* ADH. As search a motif, the sequence of amino acid -17 to amino acid 50 of the *L. brevis* ADH was used. The search program then determines all the proteins have sequence similarities. The program (reference: Altschul, Stephen F., Thomas L. Madden, Alejandro A. Schaffer, Jinghui Zhang, Zheng Zhang, Webb Miller and David J, Lipman (1997), "Gapped BLAST and PSI-BLAST: a new generation of protein data base search programs", Nucleic Acids Res. 25:3389–3402) can also fill, in gaps in order to make the similarity of sequence areas more clearly elusive. It is assumed hereby that such variation can occur also in a natural way by deletions and insertions.

Table 22 shows as a result of such a search amino acid sequences in the similarity range based on consensus for NADP-dependent dehydrogenases. Herein "sp-Q93761" means an oxido-reductase from *Caenorhabditis elegans*, "sp-P50161" means a Versicolorin reductase from *Aspergillus parasiticus*, "sp-067610" means an oxidoreductase from *Aquifex aeolicus*, "sp-P42317" means an oxidoreductase from *Bacillus subtilis* and "sp-Q49721" means an oxidoreductase from *Mycobacterium leprae*.

Table 22: Comparison of sequence areas in NADP-dependent oxidoreductases which correspond to the assumed coenzyme binding location of the ADH from *Lactobacillus brevis* (LBADH).

```
LEAD:       17  GIGLAIATKFVEEGAKVMITGRHSDVG-EKAAKSV    SEQ ID NO 22 sp-Q93761:  37  GLGKAIATTFAHLGASVAIAARRLDVD-EKTADEI    SEQ ID NO 23 sp-P50161:  20  GIGAAIAVALGERGAKVVVNYAHSREAAEKVVEQI    SEQ ID NO 24 sp-067610:  18  GIGRAIAEKLASAGSTVIITGT-SGERA-KAVAEEI   SEQ ID NO 25
```

-continued

```
sp-P42317:  14 GIRFEIAREFAREGASVIVDLR-PEAC-EKAASKL  SEQ ID NO 26 sp-Q49721:  77             EG---LI-GRHADVGA-KVAQLI   SEQ ID NO 27
```

Basic amino acid residues, which correspond to ADH from *L. brevis* in a similar spatial coordination, particularly in the positions 45 and 38 with an LBADH analog distance from the Con-sensus sequence area can be recognized. The exchange for uncharged residues as proposed by the invention should also lead in these known enzymes to a better $NAD^+$ acceptance.

In an extension of the principle of the basicity change as described herein in detail, it has further been found that, instead of the exchange of basic for uncharged amino acid residues, an exchange of basic or of uncharged amino acids for negatively charged amino acid can be made with a positive effect on the $NAD^+$ acceptance. The desired basicity reduction can be achieved, of course, also by a combination of such exchanges.

The following example 5 shows the usefulness of such an introduction of a negatively charged amino acid rest in addition to the exchange of basic by neutral amino acids in the coenzyme-sensitive area.

EXAMPLE 5
Production and Characterization of the Mutant 2/3 (A9G, G37D, R38L, K48M)

It was the object of this mutation to insert, in comparison with mutant 2, an acid amino acid into the binding location for the co-enzyme in the area 37/38. For this purpose, the mutant 2 was used which already has a high preference for $NAD^+$ with respect to $NADP^+$ and in position 37, the glycine was exchanged for aspartic acid. Consequently, the mutant 2G37D can be described with respect to the wild type as: A9G, G37D, R38L, K48M.

A) Method of Mutagenesis

For obtaining the mutant 2/3, the same methods were used as in the previous examples. Since the mutant 2/3 is a successor mutant of the mutant 2, the mutant 2 was used as template for the PCR:

G37DR38LK48M (SEQ ID NO. 13): 5' acc gac ctg cac agc gat gtt gtt gaa aaa gca gct atg agt gtc3'.(5' primer), and BRAS (3' primer), which yield the large fragment, BRS (5' primer) and G37DR38LK48Mrev (SEQ ID NO 14): 5' gac act cat agc tgc ttt ttc acc aac atc gct gtg cag gtc ggt3' (3' primer) which yield the small fragment,

TABLE 23

| | | PCR preparation (total preparation = 100 μl) | | | | |
|---|---|---|---|---|---|---|
| PCR | Template | 5' primer | 3' primer | dNTP [mM] | Buffer | DNAzyme |
| A | mutant 2 100 ng | 100 pmol G37DR38LK48M | 100 pmol BRAS | 0.2 | 10 μl | 1μl |
| B | mutant 2 100 ng | 100 pmol BRS | 100 pmol G37DR38LK4SMrev | 0.2 | 10 μl | 10 μl |

The fragments were purified and inserted into the fusion PCR at a ratio of 1:4.4 (small to large).

TABLE 24

| | | Fusion PCR | | | | |
|---|---|---|---|---|---|---|
| PCR | Template | 5' primer | 3' primer | DNTP [mM] | Buffer | DNAzyme |
| C | Fragments from PCR A and B | 100 pmol BRS | 100 pmol BRAS | 0.2 | 10 μl | 1 μl |

The product of this fusion PCR represents the complete mutant 2/3. The mutations R38L, K48, and A9G were taken over from the mutant 2. For obtaining the enzyme mutant, the gene was cloned in the vector pKU 177–214 (Boehringer) and then over-expressed in *E. coli* HB101+ (pUBS 520). The correct muta-genesis was verified by sequencing the positive clone.

B) Enzyme Production and Activity Test with $NAD^+$, $NAPD^+$, NADH, and MADPH:

Fermentation, Cell Disruption and Purification of the Enzyme Mutant 2/3:

The proliferation of the *E. coli* strain, which contains the enzyme that was changed by mutagenesis, is performed as described in examples 1 to 4.

After cell disruption and centrifuging of the cell fraction pieces, the enzyme containing supernatant crude (extract) is obtained.

In the standard enzyme test for reduction of acetophenone, with NADPH 0.032 U/mg (0.318 U/ml, 9.75 mg protein/ml) and with NADH 0.47 U/mg (4.61 U/ml; 9.75 mg protein/ml) were measured. In the reverse reaction (alcohol-oxidation) with phenyl ethanol, with $NAD^+$ a specific activity of 1.1 U/mg (10.8 U/ml); 9.75 protein/ml) were measured. With $NADP^+$, this enzyme preparation showed no activity.

With the change of the genetic information in accordance with the invention, consequently, an enzyme was obtained which accepts only NADt, but not $NADP^+$.

Attachment

Amino acid sequences of wild type and mutated $ADH_n$ from *Lactobacillus brevis* in the N-terminal area up to the 50$^{th}$ amino acid (the exchanges with respect to the wild type are marked by underlining).

A) Wild-type Enzyme

S-N-R-L-D-G-K-V-A-$I_{10}$-I-T-G-G-T-L-G-I-G-$L_{20}$-A-I-A-T-K-F-V-E-E-$G_{30}$-A-K-V-M-I-T-G-R-H-$S_{40}$-D-V-G-E-K-A-A-K-S-$V_{50}$ (SEQ ID NO 15)

B) Mutant 1:

S-N-R-L-D-G-K-V-<u>G</u>-$I_{10}$-I-T-G-G-T-L-G--I-L-G-$L_{20}$-A-I-A-T-K-F-V-E-E-$G_{30}$-A-K-V-M-I-T-G-<u>L</u>-H-$S_{40}$-D-V-G-E-<u>I</u>-A-A-K-S-$V_{50}$ (SEQ ID NO 16)

C) Mutant 1/1:

S-N-R-L-D-G-K-V-<u>G</u>-$I_{10}$-I-T-G-G-T-L-G-I-G-$L_{20}$-A-I-A-T-K-F-V-E-E-$G_{30}$-A-K-V-M-I-T-G-<u>L</u>-H-$S_{40}$-D-V-G-E-<u>M</u>-A-A-K-S-$V_{50}$ (SEQ ID NO 17)

D) Mutant 2:

S-N-R-L-D-G-K-V-<u>G</u>-$I_{10}$-I-T-G-G-T-L-G-I-G-$L_{20}$-A-I-A-T-K-F-V-E-E-$G_{30}$-A-K-V-M-I-T-G-<u>L</u>-H-$S_{40}$-D-V-G-E-K-A-A-<u>M</u>-S-$V_{50}$ (SEQ ID NO 18)

E) Mutant 2/2:

S-N-R-L-D-G-K-V-<u>G</u>-$I_{10}$-I-T-G-G-T-L-G-I-G-$L_{20}$-A-I-A-T-K-F-V-E-E-$G_{30}$-A-K-V-M-I-T-G-<u>L</u>-<u>L</u>-$S_{4P}$-D-V-G-E-K-A-A-<u>M</u>-S-$V_{50}$ (SEQ ID NO 19)

F) Mutant 2/3:

S-N-R-L-D-G-K-V-<u>G</u>-$I_{10}$-I-T-G-G-T-L-G-I-G-$L_{20}$-A-I-A-T-K-F-V-E-E-$G_{30}$-A-K-V-M-I-T-<u>D-L</u>-H-$S_{40}$-D-V-G-E-K-A-A-<u>M</u>-S-$V_{50}$ (SEQ ID NO 20)

What is claimed is:

---

We claim:

1. An (R)-specific alcohol dehydrogenase with a $k_{cat}/K_m$ for NAD$^+$ of 20 to 66 mM$^{-1}$sec$^{-1}$, a) wherein said dehydrogenase is a mutant of a wild-type (R)-specific alcohol dehydrogenase described by the following characteristics:
      (i) naturally-occurring from Lactobacillus,
      (ii) having an N-terminal sequence as set forth in SEQ ID NO:15, and
      (iii) using NADP$^{-1}$ as a cofactor for catalytic activity;
   b) wherein said mutant dehydrogenase has at least one mutation selected from the group consisting of: G37D, R38L, H39L, K45I, K45M, and K48M with respect to SEQ ID NO:15;
   c) and wherein said mutation or mutations change the alkalinity of the cofactor binding site of the mutant dehydrogenase and promote catalytic activity using NAD$^+$ as a cofactor.

2. An (R)-specific alcohol dehydrogenase according to claim 1, wherein said mutations are selected from the group consisting of:
   a) R38L and K45I as shown in the N-terminal sequence set forth in SEQ ID NO:16,
   b) R38L and K45M as shown in the N-terminal sequence set forth in SEQ ID NO:17, c) R38L and K48M as shown in the N-terminal sequence set forth in SEQ ID NO:18, d) R38L, H39L, and K48M as shown in the N-terminal sequence set forth in SEQ ID NO:19, and e) G37D, R38L, and K48M as shown in the N-terminal sequence set forth in SEQ ID NO:20.

* * * * *

SEQUENCE LISTING

```
<160> NUMBER OF SEQ ID NOS: 27

<210> SEQ ID NO 1
<211> LENGTH: 31
<212> TYPE: DNA
<213> ORGANISM: Lactobacillus brevis
<220> FEATURE:
<223> OTHER INFORMATION: primer BRS

<400> SEQUENCE: 1
gcgcgaattc atgtctaacc gtttggatgg t                             31

<210> SEQ ID NO 2
<211> LENGTH: 52
<212> TYPE: DNA
<213> ORGANISM: Lactobacillus brevis
<220> FEATURE:
<223> OTHER INFORMATION: primer BRAS

<400> SEQUENCE: 2
gcgcaagctt ctactattga gcagtgtagc caccgtcaac tacaaattca ga      52

<210> SEQ ID NO 3
<211> LENGTH: 36
<212> TYPE: DNA
<213> ORGANISM: Lactobacillus brevis
<220> FEATURE:
<223> OTHER INFORMATION: primer R38LK46I

<400> SEQUENCE: 3
accggcctgc acagcgatgt tggtgaaata gcagct                        36

<210> SEQ ID NO 4
<211> LENGTH: 36
<212> TYPE: DNA
<213> ORGANISM: Lactobacillus brevis
<220> FEATURE:
<223> OTHER INFORMATION: primer R38LK46I rev

<400> SEQUENCE: 4
agctgctatt tcaccaacat cgctgtgcag gccggt                        36

<210> SEQ ID NO 5
<211> LENGTH: 21
```

```
<212> TYPE: DNA
<213> ORGANISM: Lactobacillus brevis
<220> FEATURE:
<223> OTHER INFORMATION: primer A9G

<400> SEQUENCE: 5
ggtaaggtag gaatcattac a                                              21

<210> SEQ ID NO 6
<211> LENGTH: 21
<212> TYPE: DNA
<213> ORGANISM: Lactobacillus brevis
<220> FEATURE:
<223> OTHER INFORMATION: primer A9G rev

<400> SEQUENCE: 6
tgtaatgatt cctaccttac c                                              21

<210> SEQ ID NO 7
<211> LENGTH: 30
<212> TYPE: DNA
<213> ORGANISM: Lactobacillus brevis
<220> FEATURE:
<223> OTHER INFORMATION: primer R38LK45M

<400> SEQUENCE: 7
accggcctgc acagcgatgt tgaaatggca                                     30

<210> SEQ ID NO 8
<211> LENGTH: 33
<212> TYPE: DNA
<213> ORGANISM: Lactobacillus brevis
<220> FEATURE:
<223> OTHER INFORMATION: primer R38LK45M rev

<400> SEQUENCE: 8
tgccatttca ccaacatcgc tgtgcaggcc ggt                                 33

<210> SEQ ID NO 9
<211> LENGTH: 45
<212> TYPE: DNA
<213> ORGANISM: Lactobacillus brevis
<220> FEATURE:
<223> OTHER INFORMATION: primer R38LK48M

<400> SEQUENCE: 9
accggcctgc acagcgatgt tggtgaaaaa gcagctatga gtgtc                    45

<210> SEQ ID NO 10
<211> LENGTH: 45
<212> TYPE: DNA
<213> ORGANISM: Lactobacillus brevis
<220> FEATURE:
<223> OTHER INFORMATION: primer R38LK48M rev

<400> SEQUENCE: 10
gacactcata gctgctttt caccaacatc gctgtgcagg ccggt                     45

<210> SEQ ID NO 11
<211> LENGTH: 21
<212> TYPE: DNA
<213> ORGANISM: Lactobacillus brevis
<220> FEATURE:
<223> OTHER INFORMATION: primer R38LH39L

<400> SEQUENCE: 11
```

```
accggcctgc tcagcgatgt t                                           21
```

<210> SEQ ID NO 12
<211> LENGTH: 21
<212> TYPE: DNA
<213> ORGANISM: Lactobacillus brevis
<220> FEATURE:
<223> OTHER INFORMATION: primer R38LH39L rev

<400> SEQUENCE: 12

```
aacatcgctg agcaggccgg t                                           21
```

<210> SEQ ID NO 13
<211> LENGTH: 45
<212> TYPE: DNA
<213> ORGANISM: Lactobacillus brevis
<220> FEATURE:
<223> OTHER INFORMATION: G37DR38LK48M

<400> SEQUENCE: 13

```
accgacctgc acagcgatgt tgttgaaaaa gcagctatga gtgtc                 45
```

<210> SEQ ID NO 14
<211> LENGTH: 45
<212> TYPE: DNA
<213> ORGANISM: Lactobacillus brevis
<220> FEATURE:
<223> OTHER INFORMATION: G37DR38LK48M  rev

<400> SEQUENCE: 14

```
gacactcata gctgcttttt caccaacatc gctgtgcagg tcggt                 45
```

<210> SEQ ID NO 15
<211> LENGTH: 50
<212> TYPE: PRT
<213> ORGANISM: Lactobacillus brevis
<220> FEATURE:
<223> OTHER INFORMATION: wild-type

<400> SEQUENCE: 15

Ser Asn Arg Leu Asp Gly Lys Val Ala Ile Ile Thr Gly Gly Thr Leu
 1               5                  10                  15

Gly Ile Gly Leu Ala Ile Ala Thr Lys Phe Val Glu Glu Gly Ala Lys
            20                  25                  30

Val Met Ile Thr Gly Arg His Ser Asp Val Gly Glu Lys Ala Ala Lys
        35                  40                  45

Ser Val
    50

<210> SEQ ID NO 16
<211> LENGTH: 50
<212> TYPE: PRT
<213> ORGANISM: Lactobacillus brevis
<220> FEATURE:
<223> OTHER INFORMATION: mutant 1

<400> SEQUENCE: 16

Ser Asn Arg Leu Asp Gly Lys Val Gly Ile Ile Thr Gly Gly Thr Leu
 1               5                  10                  15

Gly Ile Gly Leu Ala Ile Ala Thr Lys Phe Val Glu Glu Gly Ala Lys
            20                  25                  30

Val Met Ile Thr Gly Leu His Ser Asp Val Gly Glu Ile Ala Ala Lys
        35                  40                  45

Ser Val
    50

<210> SEQ ID NO 17
<211> LENGTH: 50
<212> TYPE: PRT
<213> ORGANISM: Lactobacillus brevis
<220> FEATURE:
<223> OTHER INFORMATION: mutant 1/1

<400> SEQUENCE: 17

Ser Asn Arg Leu Asp Gly Lys Val Gly Ile Ile Thr Gly Gly Thr Leu
 1               5                  10                  15

Gly Ile Gly Leu Ala Ile Ala Thr Lys Phe Val Glu Glu Gly Ala Lys
            20                  25                  30

Val Met Ile Thr Gly Leu His Ser Asp Val Gly Glu Met Ala Ala Lys
        35                  40                  45

Ser Val
    50

<210> SEQ ID NO 18
<211> LENGTH: 50
<212> TYPE: PRT
<213> ORGANISM: Lactobacillus brevis
<220> FEATURE:
<223> OTHER INFORMATION: mutant 2

<400> SEQUENCE: 18

Ser Asn Arg Leu Asp Gly Lys Val Gly Ile Ile Thr Gly Gly Thr Leu
 1               5                  10                  15

Gly Ile Gly Leu Ala Ile Ala Thr Lys Phe Val Glu Glu Gly Ala Lys
            20                  25                  30

Val Met Ile Thr Gly Leu His Ser Asp Val Gly Glu Lys Ala Ala Met
        35                  40                  45

Ser Val
    50

<210> SEQ ID NO 19
<211> LENGTH: 50
<212> TYPE: PRT
<213> ORGANISM: Lactobacillus brevis
<220> FEATURE:
<223> OTHER INFORMATION: mutant 2/2

<400> SEQUENCE: 19

Ser Asn Arg Leu Asp Gly Lys Val Gly Ile Ile Thr Gly Gly Thr Leu
 1               5                  10                  15

Gly Ile Gly Leu Ala Ile Ala Thr Lys Phe Val Glu Glu Gly Ala Lys
            20                  25                  30

Val Met Ile Thr Gly Leu Leu Ser Asp Val Gly Glu Lys Ala Ala Met
        35                  40                  45

Ser Val
    50

<210> SEQ ID NO 20
<211> LENGTH: 50
<212> TYPE: PRT
<213> ORGANISM: Lactobacillus brevis
<220> FEATURE:
<223> OTHER INFORMATION: mutant 2/3

<400> SEQUENCE: 20

```
Ser Asn Arg Leu Asp Gly Lys Val Gly Ile Ile Thr Gly Gly Thr Leu
 1               5                  10                  15

Gly Ile Gly Leu Ala Ile Ala Thr Lys Phe Val Glu Glu Gly Ala Lys
             20                  25                  30

Val Met Ile Thr Asp Leu His Ser Asp Val Gly Glu Lys Ala Ala Met
         35                  40                  45

Ser Val
     50

<210> SEQ ID NO 21
<211> LENGTH: 50
<212> TYPE: PRT
<213> ORGANISM: Lactobacillus brevis
<220> FEATURE:
<223> OTHER INFORMATION: N-terminal area

<400> SEQUENCE: 21

Ser Asn Arg Leu Asp Gly Lys Val Ala Ile Ile Thr Gly Gly Thr Leu
 1               5                  10                  15

Gly Ile Gly Leu Ala Ile Ala Thr Lys Phe Val Glu Glu Gly Ala Lys
             20                  25                  30

Val Met Ile Thr Gly Arg His Ser Asp Val Gly Glu Lys Ala Ala Lys
         35                  40                  45

Ser Val
     50

<210> SEQ ID NO 22
<211> LENGTH: 34
<212> TYPE: PRT
<213> ORGANISM: Lactobacillus brevis
<220> FEATURE:
<223> OTHER INFORMATION: LBADH

<400> SEQUENCE: 22

Gly Ile Gly Leu Ala Ile Ala Thr Lys Phe Val Glu Glu Gly Ala Lys
 1               5                  10                  15

Val Met Ile Thr Gly Arg His Ser Asp Val Gly Glu Lys Ala Ala Lys
             20                  25                  30

Ser Val

SEQ ID NO 23
<211> LENGTH: 34
<212> TYPE: PRT
<213> ORGANISM: Lactobacillus brevis
<220> FEATURE:
<223> OTHER INFORMATION: sp-Q93761

<400> SEQUENCE: 23

Gly Leu Gly Lys Ala Ile Ala Thr Thr Phe Ala His Leu Gly Ala Ser
 1               5                  10                  15

Val Ala Ile Ala Ala Arg Arg Leu Asp Val Leu Glu Lys Thr Ala Asp
             20                  25                  30

Glu Ile

<210> SEQ ID NO 24
<211> LENGTH: 35
<212> TYPE: PRT
<213> ORGANISM: Lactobacillus brevis
<220> FEATURE:
<223> OTHER INFORMATION: sp-P50161
```

```
<400> SEQUENCE: 24

Gly Ile Gly Ala Ala Ile Ala Val Ala Leu Gly Glu Arg Gly Ala Lys
 1               5                  10                  15
Val Val Val Asn Tyr Ala His Ser Arg Glu Ala Ala Glu Lys Val Val
            20                  25                  30
Glu Gln Ile
        35

<210> SEQ ID NO 25
<211> LENGTH: 34
<212> TYPE: PRT
<213> ORGANISM: Lactobacillus brevis
<220> FEATURE:
<223> OTHER INFORMATION: sp-O067610

<400> SEQUENCE: 25

Gly Ile Gly Arg Ala Ile Ala Glu Lys Leu Ala Ser Ala Gly Ser Thr
 1               5                  10                  15
Val Ile Ile Thr Gly Thr Ser Gly Glu Arg Ala Lys Ala Val Ala Glu
            20                  25                  30
Glu Ile

<210> SEQ ID NO 26
<211> LENGTH: 33
<212> TYPE: PRT
<213> ORGANISM: Lactobacillus brevis
<220> FEATURE:
<223> OTHER INFORMATION: sp-P42317

<400> SEQUENCE: 26

Gly Ile Arg Phe Glu Ile Ala Arg Glu Phe Ala Arg Glu Gly Ala Ser
 1               5                  10                  15
Val Ile Val Asp Leu Arg Pro Gly Ala Cys Glu Lys Ala Ala Ser Lys
            20                  25                  30
Leu

<210> SEQ ID NO 27
<211> LENGTH: 18
<212> TYPE: PRT
<213> ORGANISM: Lactobacillus brevis
<220> FEATURE:
<223> OTHER INFORMATION: sp-Q49721

<400> SEQUENCE: 27

Glu Gly Leu Ile Gly Arg His Ala Asp Val Gly Ala Lys Val Ala Gln
 1               5                  10                  15
Leu Ile
```